(12) United States Patent
Katoh et al.

(10) Patent No.: US 6,604,855 B2
(45) Date of Patent: Aug. 12, 2003

(54) FLUOROSCOPIC RADIOGRAPHING CARRIER APPARATUS

(75) Inventors: Mikihiko Katoh, Kyoto (JP); Katsuhiro Masuo, Kusatsu (JP)

(73) Assignee: Shimadzu Corporation, Kyoto (JP)

( * ) Notice: Subject to any disclaimer, the term of this patent is extended or adjusted under 35 U.S.C. 154(b) by 215 days.

(21) Appl. No.: 09/863,364

(22) Filed: May 24, 2001

(65) Prior Publication Data
US 2002/0006184 A1 Jan. 17, 2002

(30) Foreign Application Priority Data
Jul. 14, 2000 (JP) .................................. 2000-213679

(51) Int. Cl.[7] .................................................. H05G 1/02
(52) U.S. Cl. ........................................ 378/196; 378/197
(58) Field of Search ............................... 378/196, 197, 378/198, 42, 177, 181

(56) References Cited

U.S. PATENT DOCUMENTS 4,139,776 A * 2/1979 Hellstrom .................... 378/25
5,023,899 A * 6/1991 Ohlson ........................ 378/196
5,185,777 A * 2/1993 Hasegawa .................... 378/176

* cited by examiner

Primary Examiner—Louis Arana
(74) Attorney, Agent, or Firm—Kanesaka & Takeuchi

(57) ABSTRACT

An X-ray tube device is rotated to a projected portion in a subject by a rotating mechanism for the X-ray tube device according to an operation for an oblique fluoroscopy. A CPU recognizes information about a rotating angle and rotation speed, and a stand for the X-ray tube is moved along a longitudinal direction of a top plate by a driving mechanism for the stand according to the information. An X-ray image detector disposed under the top plate is moved in a direction opposite to the movement of the stand to a corresponding position of the X-ray tube device by a driving mechanism for the X-ray image detector. The X-ray tube device, the projected portion in the subject and the X-ray image detector are always arranged in a straight line by the CPU and the independent driving mechanisms. A tomography may also be carried out by moving continuously the X-ray tube device and the X-ray image detector parallel to the top plate in the opposite directions.

5 Claims, 2 Drawing Sheets

FLUOROSCOPIC RADIOGRAPHING CARRIER APPARATUS

BACKGROUND OF THE INVENTION AND RELATED ART STATEMENT

The present invention relates to a fluoroscopic radiographing carrier apparatus or stand, which is especially used for oblique fluoroscopy, oblique radiography, and linear tomography.

When fluoroscopic radiography of a subject or patient to be examined is carried out by X-rays, the subject is put on a top plate of an X-ray fluoroscopic radiographing carrier apparatus or stand, and an X-ray tube device and an X-ray image detector provided on the opposite side of the top plate relative to the X-ray tube device, is usually used. In the X-ray fluoroscopic radiographing carrier apparatus, X-rays passing through a portion of the subject are recorded on an X-ray image detector (such as an X-ray radiographing film device, an image intensifier and a semiconductor flat panel image pickup device), or displayed on a TV monitor by converting data to electric signals and forming pictures, or memorized.

In order to diagnose or determine a location and size of an interested portion (affected part) in the subject, oblique fluoroscopy or oblique radiography, in which a direction of incidence of X-rays relative to the subject is set obliquely, is carried out. A plurality of tomograms with varying a height of a cutting plane of the subject is also taken.

An image obtained by simple radiography is displayed in a single film in a condition that all the tissues and organs of the portions taken by radiographing in the direction of the X-rays are overlapped. In tomography, an X-ray image on a plane which is intended to see is only showed clearly, and X-ray images of the portions front and behind the plane is out of focus. Accordingly, the X-ray image close to the cutting plane of the subject is only obtained.

In the tomography, a fault image is obtained by moving two among the X-ray tube device, the subject and the X-ray image detector, while synchronizing with each other. Usually, the subject is fixed, and the X-ray tube device and the X-ray image detector, such as a film, are moved.

An X-ray fluoroscopic radiographing carrier apparatus or stand which is used for oblique fluoroscopy and radiography is shown in FIG. 4. The X-ray fluoroscopic radiographing carrier 1 apparatus has an X-ray tube device 1, a stand 7 which supports the X-ray tube device 1, and an X-ray image detector 3 which detects X-rays passing through a subject or patient 8. The X-ray tube device 1 rotates around a fulcrum 10, and an oblique incident angle to the subject 8 may be changeable. Accordingly, the oblique fluoroscopy and radiography may be carried out by using the X-ray tube device 1 and the X-ray image detector 3 disposed under a top plate 4.

In the X-ray fluoroscopic radiographing carrier apparatus, since the X-ray image detector 3 is not moved sufficiently, tomography can not be carried out. The X-ray tube device 1 can be, however, set obliquely by inclining the stand 7, and the stand 7 with the X-ray tube device 1 and the X-ray image detector 3 may be moved parallel to the top plate 4. Furthermore, the top plate 4 on which the subject 8 is placed, may be moved along the longitudinal direction of the top plate.

A conventional X-ray fluoroscopic radiographing carrier apparatus or stand is composed as described above, but when the subject 8 is seen through the fluoroscope from a front, a point A is projected at a center of the X-ray image detector 3. However, when the X-ray tube 1 is located at an oblique position, a point B in the subject 8 is projected at the center of the X-ray image detector 3 and the point A in the subject 8 is projected at an edge of the X-ray image detector 3. Since an objective radiographing point is shifted for a distance corresponding to the oblique incident angle by changing the angle, the fluoroscopy and the radiography for the objective portion can not be achieved. Accordingly, it is necessary to adjust a position of the portion to be photographed in the subject by moving the top plate 4 or the stand 7 with the X-ray tube device 1 and the X-ray image detector 3 again, and it causes the problem of lowering an efficiency of diagnosis.

The present invention has been made in view of such circumstances as described above, and an object of the invention is to provide an X-ray fluoroscopic radiographing carrier apparatus or stand, wherein even if oblique fluoroscopy and oblique radiograph in which X-ray is obliquely irradiated to a subject are carried out, a projected image on an X-ray image detector is not shifted.

Further objects and advantages of the invention will be apparent from the following description of the invention.

SUMMARY OF THE INVENTION

In order to achieve the purpose as described above, an X-ray fluoroscopic radiographing carrier apparatus of the invention includes an X-ray tube device which rotates and inclines along a body axis of a subject, a stand which supports the X-ray tube device, and an X-ray image detector disposed on the side opposite to a top plate relative to the X-ray tube device. Each of the X-ray tube device, the stand and the X-ray image detector is independently moved by independent driving control means, so that oblique fluoroscopy, oblique radiography and linear tomography may be carried out.

The X-ray fluoroscopic radiographing carrier apparatus of the invention has means for moving the X-ray tube device and the X-ray image detector parallel to the top plate in order to correct a shift of a position of the projected portion in the subject, which occurs when the X-ray tube device is rotated and inclined and an oblique angle is changed.

The X-ray fluoroscopic radiographing carrier apparatus of the invention is formed as described above. Since each of the X-ray tube device, the stand and the X-ray image detector is independently moved by independent drive portions and control portions, the X-ray can always be irradiated to an interested portion in the subject, which is intended to project, in spite of changing of the oblique angle. Furthermore, since the X-ray image detector can be moved for a distance corresponding to the oblique angle, the interested portion in the subject is always projected to a center of the X-ray image detector.

While the shift of the position of the projected portion in the subject, which occurs when the X-ray tube device is rotated and inclined and the oblique angle is changed, is corrected by moving the X-ray image detector, the X-ray tube device 3 attached to the stand and the X-ray image detector 9 can be moved parallel to the top plate interposed therebetween and in the opposite directions. Accordingly, a tomography by linear moving system can be carried out.

DETAILED DESCRIPTION OF PREFERRED EMBODIMENTS

Figure 1:
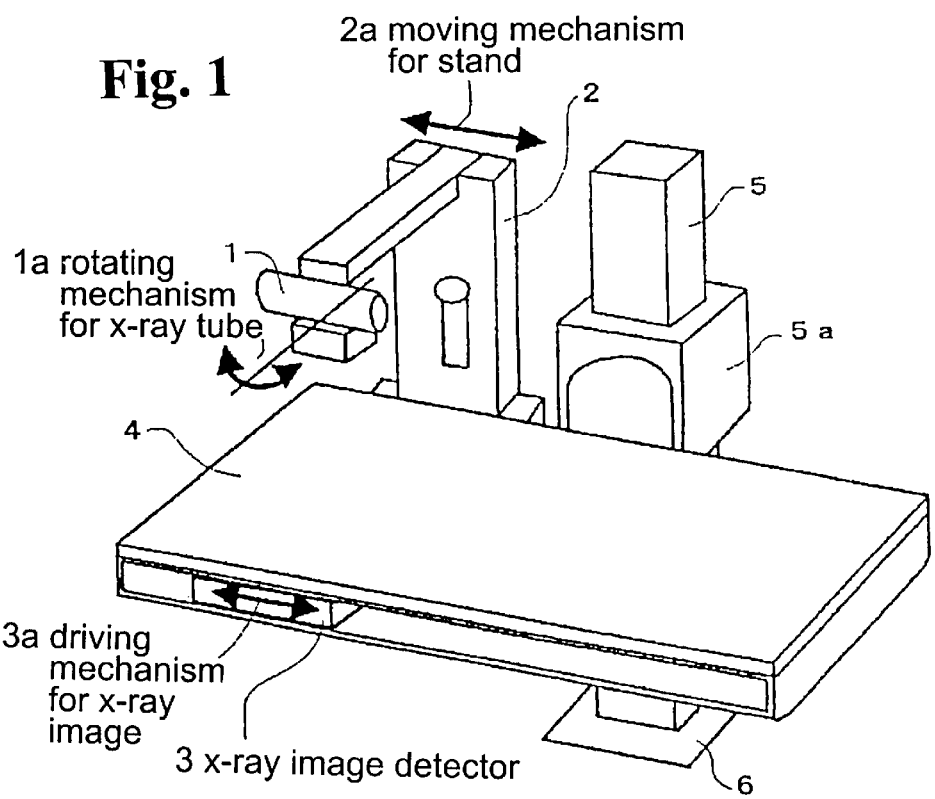
FIG. 1 is an explanatory perspective view for explaining an example of an X-ray fluoroscopic radiographing carrier apparatus or stand of the invention.

An embodiment of an X-ray fluoroscopic radiographing carrier apparatus of the present invention is explained with reference to FIG. 1. FIG. 1 is an explanatory perspective view of the X-ray fluoroscopic radiographing carrier apparatus or stand of the present invention, in which fluoroscopy and radiograph for oblique X-ray irradiation is carried out, and also, a fault image can be taken by moving linearly an X-ray tube device 1 and an X-ray image detector 3 parallel to each other.

The X-ray fluoroscopic radiographing carrier apparatus or stand includes the X-ray tube device 1 which rotates at an end of a stand 2, wherein the stand 2 supports the X-ray tube device 1 and is moved parallel to a top plate 4; the X-ray image detector 3 which is moved under the top plate 4 according to a movement of the X-ray tube device 1 and detects X-rays passing through a subject or patient; and driving control means which includes a rotational driving portion 12 for X-ray tube, a rotation control portion 13 for X-ray tube, a driving portion 14 for stand, a control portion 15 for stand, a detecting and driving portion 16 for X-ray image, a detecting control portion 17 for X-ray image, and a central processing unit (CPU) 18. In the driving control means, the oblique fluoroscopy and oblique radiography may be carried out by the X-ray tube device 1 which moves parallel to the top plate 4 and rotates relative to the subject or patient, and the X-ray image detector 3 which is moved in response to the X-ray tube device in the opposite direction relative to the movement of the X-ray tube device 1 parallel to the top plate 4.

The X-ray fluoroscopic radiographing carrier apparatus or stand has a main stand 5 set up on a base stand 6 with a support portion 5a, wherein the support portion 5a supports the top plate 4, the stand 2 with an arm whose end is connected to the X-ray tube device 1, and the X-ray image detector 3 provided under the top plate 4. The stand 2 is moved along the longitudinal direction of the top plate 4 by an electric motor in a driving mechanism 2a for the stand portion, and the X-ray tube device 1 is rotated to a projected portion on the subject by a rotating mechanism 1a for the X-ray tube, which includes an electric motor provided at the end of the arm of the stand 2, according to the movement of the stand 2.

The X-ray image detector 3 is moved in the direction opposite to the movement of the X-ray tube device 1 to be located in the position corresponding to the X-ray tube device 1 by an electric motor in a driving mechanism 3a for the X-ray image detector. In this state, the oblique fluoroscopy or oblique radiography is carried out. A tomography can also be carried out by moving continuously the X-ray tube device 1 and the X-ray image detector 3 parallel to the top plate in the opposite directions.

Figure 2:
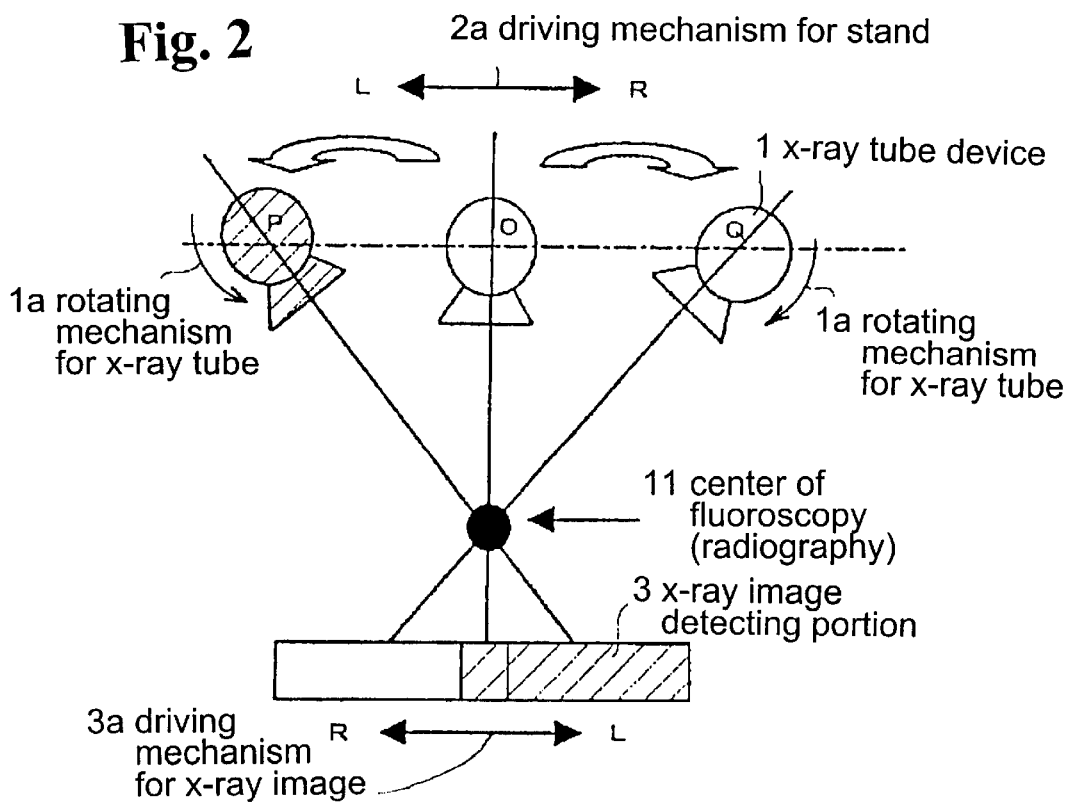
FIG. 2 is a view for explaining a principle of a movement at an oblique angle for the X-ray fluoroscopic radiographing carrier apparatus of the invention.

Movements of the drive portions in the X-ray fluoroscopic radiographing carrier apparatus are shown in FIG. 2. In case that the oblique fluoroscopy or radiography is carried out, the X-ray tube device 1 rotates counterclockwise by the rotating mechanism 1a for the X-ray tube, and at the same time, the stand 2 is moved to P in the direction of L by the driving mechanism 2a for the stand according to the rotation of the X-ray tube device 1. On the other hand, the X-ray image detector 3 is moved in the direction opposite to the movement of the stand, so that the center of the X-ray image detector 3 is located on the opposite side of a center 11 for the fluoroscopy or radiography as a fulcrum to the X-ray tube device 1 by the driving mechanism 3a for the X-ray image detector.

When the X-ray tube device 1 rotates clockwise, the stand 2 is moved to Q in the direction of R. The X-ray image detector 3 is moved in the opposite direction of the movement of the stand 2. The movements are controlled by each of the independent drive and control portions of the X-ray tube device 1, the stand 2 and the X-ray image detector 3 according to an order from the CPU 18, so that the shift of the X-ray image on the X-ray image detector 3 due to the rotation of the X-ray tube device 1 can be corrected.

In case that a direct linear tomography is carried out, the fault image is taken by moving the X-ray tube device 1 and the X-ray image detector 3 parallel to the top plate 4 relative to the center 11 for the fluoroscopy or radiography as a fulcrum, which is set above the top plate 4. The cutting plane of the fault is parallel to the top plate 4 and includes the center 11 for the fluoroscopy or radiography. The cutting plane can be set by a computer on a control desk.

Figure 3:
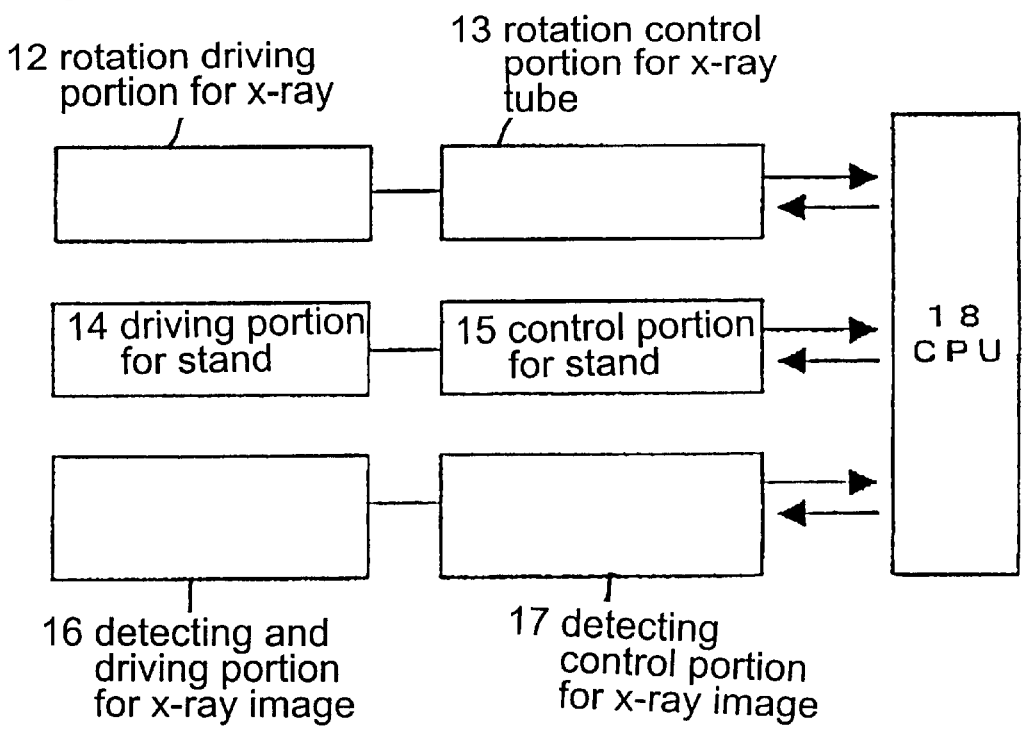
FIG. 3 is a block diagram for controlling the X-ray fluoroscopic radiographing carrier apparatus of the invention.
Figure 4:
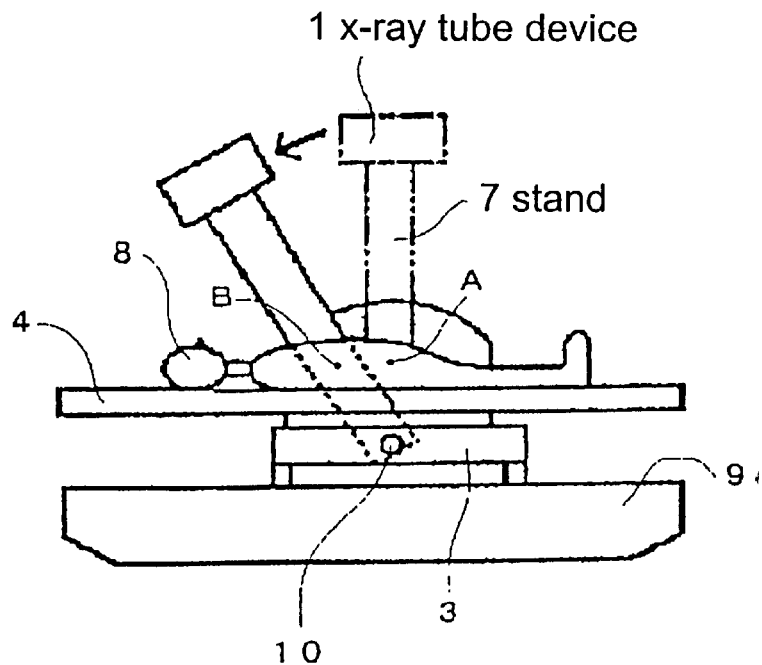
FIG. 4 is an explanatory view of a conventional X-ray fluoroscopic radiographing carrier apparatus.

A block diagram for controlling the X-ray fluoroscopic radiographing carrier apparatus of the invention is shown in FIG. 3. The driving control means for the oblique fluoroscopy has the rotation driving portion 12 for X-ray to rotate the X-ray tube device itself, the rotation control portion 13 for X-ray tube, the drive portion 14 for stand to move the stand parallel to the top plate 4, the control portion 15 for stand, the detecting and driving portion 16 for X-ray image to move the X-ray image detector 3 under the top plate 4 in the direction opposite to the movement of the X-ray tube device 1, the detecting control portion 17 for the X-ray image, and the CPU 18. The CPU 18 controls the independent drive and control portions of the X-ray tube device 1, the stand 2 and the X-ray image detector 3 so that the shift of the X-ray image on the X-ray image detector 3 by rotating the X-ray tube device 1 is corrected.

The X-ray image detector 3 is a sensor which receives X-rays passing through the subject or patient and forms an X-ray image, and is an image pickup device for an image intensifier or a semi-conductor flat panel. There are two types of the image pickup device for the semi-conductor flat panel. The one type has an X-ray conversion film which converts X-rays to light, photodiode arrays which are arranged in a matrix immediately under the film, and switching components connected to the respective photodiode arrays. After X-ray irradiation, signal charges stored in the respective picture elements are read to form the X-ray image by sequentially switching the switching components.

The other type has radiation sensor arrays formed of a conversion film, which responds to radiations and directly outputs charge signals corresponding to the incident radiation amount, electrodes disposed in a matrix form immediately under the radiation sensor arrays, and switching components connected to the electrodes, respectively. At the time of irradiation, signal charges stored in the respective pixels are read by switching the switching components in sequence to form the X-ray image.

In both types, data storing device may be included, and an image may be made by the OFF-line. The signal may also be sent from the X-ray image detector 3 of the radiography device by the ON-line. When the semi-conductor flat panel is used, since it does not need a large space required by the image intensifier or the like, the projection device can be made compact.

An operation of the X-ray fluoroscopic radiographing carrier apparatus or stand of the present invention is explained. The subject or patient 8 is put on the top plate 4. The stand 2 is moved by operating a switch for moving the stand 2 provided on the control desk, and the X-ray tube device 1 is set above an interested portion in the subject 8. A positioning is carried out by a light sight device of a collimator disposed on the X-ray tube device 1.

An operator operates a switch for a right oblique angle or a left oblique angle provided on the control desk. According to the operation, the CPU 18 actuates the rotation driving portion 12 for the X-ray tube device through the rotation control portion 13 for the X-ray tube device 13, to thereby rotate the X-ray tube device 1. The CPU 18 receives or recognizes the rotation speed and the rotating angle of the X-ray tube device 1, and at the same time, calculates a horizontal moving distance and speed of the stand 2 by the information about the rotation speed and rotating angle. According to the result of the calculation, the CPU 18 operates the driving portion 14 for the stand through the control portion 15 for the stand to thereby move the stand 2.

Also, the CPU 18 calculates a horizontal moving distance and speed of the X-ray image detector 3 by the information as described above. The CPU 18 operates the detecting and driving portion 16 for the X-ray image through the detecting control portion 17 for the X-ray image, to thereby move the X-ray image detector 3 horizontally in the opposite direction of the movement of the stand 2. By the movements, the X-ray tube device 1, the interested portion in the subject 8 and the X-ray image detector 3 are arranged in a straight line at any operated oblique angle. In this situation, X-ray on-button is pushed, and the fluoroscopy or radiography is carried out.

In the example as described above, the explanation is made by the control of the CPU 18. However, in case that a moving length of the stand 2 or the X-ray image detector 3 is not enough to correct the shift of a position of the projected portion in the subject, the top plate can be moved to correct the shift of a position of the projected portion in the subject.

The center for the fluoroscopy or radiography may be located at any position in the upper or lower direction relative to the top plate 4 by changing the moving length of the stand 2 and the X-ray image detector 3.

The X-ray fluoroscopic radiographing carrier apparatus or stand of the present invention is constructed as described above.

When the oblique fluoroscopy or radiography is carried out with irradiating X-rays obliquely to the subject, if the switch for an oblique angle provided on the control desk is operated, the X-ray tube device 1 is rotated by the control portion according to the order from the CPU disposed in the control portion. The CPU detects or recognizes the rotation speed and the rotating angle of the X-ray tube device, and also, makes the stand for supporting the X-ray tube device move parallel to the top plate while calculating the moving distance and speed of the stand. On the other hand, the X-ray image detector is moved in the opposite direction of the movement of the stand while calculating the moving distance and speed of the X-ray image detector.

By the movements, the X-ray tube device, the interested portion in the subject and the X-ray image detector are arranged in a straight line in the operated oblique angle, and the interested portion in the subject can always be located in radiography at the center of the X-ray image detector. Accordingly, it is not necessary for photographing the portion again, and an efficiency of diagnosis can be improved.

While the shift of the X-ray image of the subject occurred in the oblique angle operation is corrected by changing the movement of the X-ray detector, the X-ray device attached to the stand and the X-ray image detector can be moved in the opposite directions parallel to the top plate interposed therebetween. Accordingly, tomography by linear movement can be carried out.

While the invention has been explained with reference to the specific embodiments of the invention, the explanation is illustrative and the invention is limited only by the appended claims.

What is claimed is:

1. An X-ray fluoroscopic radiographing carrier apparatus, comprising:
    an X-ray tube device movably disposed relative to a subject to be examined,
    a stand attached to the X-ray tube device for supporting the same,
    a top plate situated under the X-ray tube device,
    an X-ray image detector movably disposed under the top plate, and
    driving control means electrically connected to the X-ray tube device, the stand and the X-ray image detector for rotating the X-ray tube device and moving the stand and the X-ray image detector independently to carry out a linear tomography, said driving control means controlling the X-ray tube device to change an angle relative to the top plate, the stand to move in one linear direction along the top plate, and the X-ray image detector to move in a direction opposite to the one linear direction so that X-ray irradiated from the X-ray tube device passes through a point as a fulcrum and the X-ray passing through the point is always located on a predetermined point of the X-ray image detector.

2. An X-ray fluoroscopic radiographing carrier apparatus according to claim 1, further comprising a mechanism attached to the X-ray tube device and the X-ray image detector for moving the X-ray tube device and the X-ray image detector parallel to the top plate to correct a shift of a position of a projected portion in the subject occurred by rotating the X-ray tube device.

3. An X-ray fluoroscopic radiographing carrier apparatus according to claim 2, wherein the X-ray tube device and the X-ray image detector are associated such that when the X-ray tube device and the X-ray image detector are moved relative to the subject, a center of movements on the straight line is located at one portion above the top plate.

4. An X-ray fluoroscopic radiographing carrier apparatus according to claim 2, wherein the X-ray image detector has a semi-conductor flat panel.

5. An X-ray fluoroscopic radiographic carrier apparatus according to claim 2, wherein the top plate is moveable.

* * * * *